(12) United States Patent
Staton et al.

(10) Patent No.: US 7,877,212 B2
(45) Date of Patent: Jan. 25, 2011

(54) METHODS AND COMPOSITIONS FOR ASSESSING PARTIALLY SATURATED PIXEL SIGNALS

(75) Inventors: Kenneth L. Staton, San Carlos, CA (US); John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1037 days.

(21) Appl. No.: 10/912,661

(22) Filed: Aug. 4, 2004

(65) Prior Publication Data

US 2006/0031019 A1 Feb. 9, 2006

(51) Int. Cl.
*G06K 9/46* (2006.01)
*G06K 9/60* (2006.01)
*G06K 9/52* (2006.01)
*G01N 33/48* (2006.01)

(52) U.S. Cl. .......................................... 702/19; 382/194
(58) Field of Classification Search ........................ None
See application file for complete search history.

(56) References Cited

U.S. PATENT DOCUMENTS 6,730,521 B1 * 5/2004 Cassells ...................... 436/523
6,909,459 B2 * 6/2005 Watson et al. ............ 348/229.1

OTHER PUBLICATIONS

Barducci et al., A New Alogorithm for Temperature and Spectral Emissivity Retrieval Over Active Fires in the TIR Spcetral Range, Jul. 7, 2004, IEEE Transactions on Geoscience and Remote Sensing, vol. 42, pp. 1521-1529.*
Cheung et al. "Making and Reading Microarrays" Nature America Inc- Nature Genetics Supplement (1999) 21:15-18.

* cited by examiner

*Primary Examiner*—Marjorie Moran
*Assistant Examiner*—Jason M Sims

(57) ABSTRACT

Methods for producing data for a partially saturated pixel produced during scanning of a chemical array are provided. In general, an analog signal for a partially saturated pixel is sampled to obtain a set of non-saturated digital signals and a set of saturated digital signals. The saturated digital signals are then processed to produce data for the pixel. Also provided are computer program products comprising programming for performing the subject methods, and a chemical array scanner containing this programming. The invention finds use in a variety of different applications, including both genomics and proteomics applications.

11 Claims, 4 Drawing Sheets

METHODS AND COMPOSITIONS FOR ASSESSING PARTIALLY SATURATED PIXEL SIGNALS

BACKGROUND OF THE INVENTION

Arrays of surface-bound binding agents may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate, such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In certain instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

For each pixel of a scan, a light detector (e.g., a photomultiplier tube) typically detects light emitted from the surface of a microarray, and outputs an analog signal line that changes in amplitude according to the amount of emitted light entering the detector. This analog signal is usually sampled and digitized using an analog-to-digital converter (A/D converter) and integrated using a digital signal processor (DSP) to provide data, e.g., a numerical evaluation of the brightness of the pixel. This data is usually stored and analyzed at a later date.

However, current data processing methodologies are limited in their capacity to obtain reliable data from every pixel of a scan because there is a limitation to the range of amplitudes detectable. Accordingly, for many bright areas of a scan, the analog signal produced by a light detection system may be partially or fully "saturated", i.e., at the maximum amplitude. Because of this limitation, the output signal of a detection system may not always accurately represent the amount of light entering the detection system if the amount of light entering the light detection system exceeds the detection limits of the detection system's detection, signal amplification and conversion circuitry. Despite this limitation, saturated and partially saturated signals are typically digitized and integrated using similar methods to those for non-saturated signals, leading to inaccurate (usually under-estimated) data for pixels with saturated or partially saturated signals.

Accordingly, there is a great need for a signal integration system that can increase the accuracy of data obtained from a saturated or partially saturated pixel. The present invention meets this, and other, needs.

Literature of interest includes: published U.S. Patent Applications: 20030168579, 20030165871, 20040064264, 20040023224, 20040021911, 20030203371 and 20030168579; and Cheung et al., Nature Genetics 1999, 21: 15-19.

SUMMARY OF THE INVENTION

Methods for producing data for a partially saturated pixel produced during scanning of a chemical array are provided. In general, an analog signal for a partially saturated pixel is sampled to obtain a set of non-saturated digital signals and a set of saturated digital signals. The saturated digital signals are then processed to produce data for the pixel. Also provided are computer program products comprising programming for performing the subject methods, and a chemical array scanner containing this programming. The invention finds use in a variety of different applications, including both genomics and proteomics applications.

In one embodiment, the invention provides method for producing data for a partially saturated pixel during scanning of a chemical array. This method generally includes: sampling an analog signal for a partially saturated pixel to provide a set of non-saturated digital signals and a set of saturated digital signals; and processing said non-saturated to produce data for said partially saturated pixel. In certain embodiments, the method may comprise estimating said saturated digital signals by extrapolating said non-saturated digital signals to provide a set of estimated digital signals The chemical array used in the method may be a nucleic acid array or a polypeptide array, for example.

In certain embodiments, the analog signal for a partially saturated pixel is sampled at least about 10 times.

In certain embodiments, the method further involves employing a current to voltage converter that converts an analog current representing intensity of said pixel to an analog voltage signal.

The method may also comprise tagging said data with an identifier to indicate that said data is derived from a partially saturated pixel.

The data may be stored on a computer-readable medium.

In another embodiment, the invention provides a chemical array scanner. This scanner generally includes: a laser excitation system; a detection system that produces an analog signal representative of emitted light from the surface of an array; a system for performing the above method; and a storage medium for storing data produced by the method. In addition, the scanner may contain an analog-to-digital signal converter; and a digital signal processor for integrating the non-saturated and the estimated digital signals. The storage medium may be computer memory.

The invention also provides a computer-readable medium comprising: programming products for execution by a digital signal processor to produce data for a pixel represented by saturated and non-saturated digital signals, the programming comprising: instructions for estimating the saturated digital signals by extrapolating the non-saturated digital signals; and instructions for integrating the estimated digital signals the said non-saturated digital signals to produce data for the pixel. The computer-readable medium may further comprise instructions for executing the programming when a partially-saturated pixel is detected.

The output of the programming may be data for a partially saturated pixel, and the output may be tagged to indicate that said data is estimated from a set of saturated and non-saturated digital signals.

The invention also provides a computer containing the above computer-readable medium and a chemical array scanner comprising or in communication with that computer.

The invention also provides a method of assaying a sample. This method comprises: (a) contacting the sample with a chemical array of two or more chemical ligands immobilized on a surface of a solid support; and (b) reading the array with a chemical array scanner according to the above to obtain data. Step (b) in this method may include: sampling a partially saturated analog signal to provide a set of non-saturated digital signals and a set of saturated digital signals for said partially saturated pixel; and processing the non-saturated signals to produce data for a partially saturated pixel. Step (b) of this method may comprise estimating the saturated digital signals by extrapolating the non-saturated digital signals to provide a set of estimated digital signals In certain embodiments, the array may be a nucleic acid or polypeptide array.

The invention also provides a method including transmitting a result obtained from any of the above-described methods from a first location to a remote location, and a method including receiving data representing data obtained by any of the above-described methods.

The invention also provides a kit for use in a chemical array optical scanner, containing: (a) a computer-readable medium according to the above; and (b) at least one chemical array.

DEFINITIONS

Figure 1:
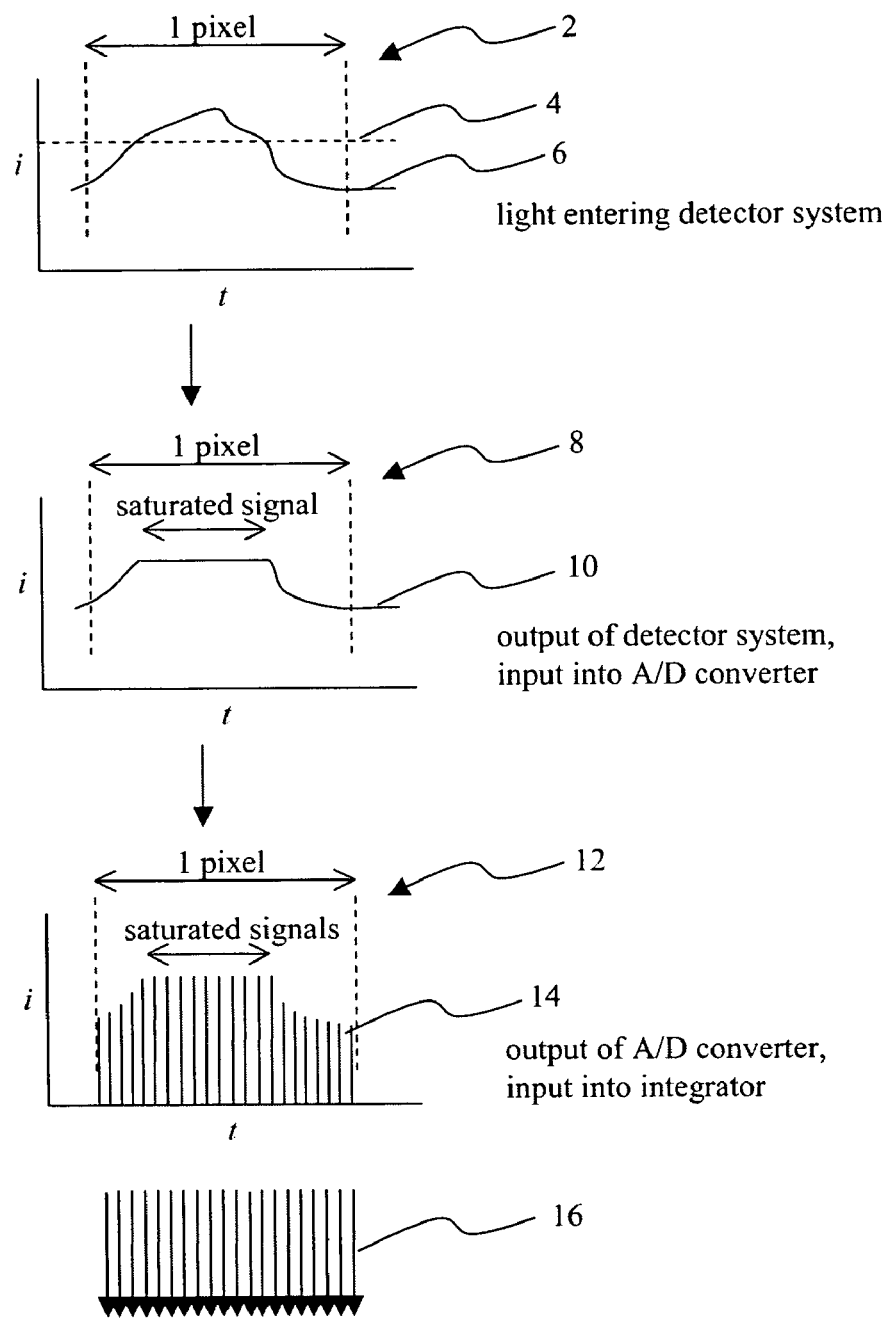
FIG. 1 schematically illustrates one embodiment of the signal acquisition, processing and integration methods described herein.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), polypeptides (which term is used to include peptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array" or "chemical array" includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In certain embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). If a device is "in communication with" another device, the devices are capable of transmitting or data or instructions to each other. Such devices may be networked to each other. "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and 6,355,934.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of a pixel signal to determine the brightness of a corresponding area present on the surface of an object scanned.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may programmed or hard wired to perform one or more mathematical functions, such as those described below. In certain embodiments, a signal processor may "integrate" a set of digital signals (e.g., a set of digital signals representing an analog signal or a digitized version of an analog signal). By "integrating" is meant that a set of digital signals is input into a signal processor and the signal processor provides an output signal, usually but not always a single output signal, that represents the set of input signals. In many embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled and digitized) prior to integration. For example, if an analog signal for a pixel is to be integrated, the signal is first sampled and digitized to provide a set of digital signals, and those digital signals are integrated by a signal processor to provide an output signal, usually but not always a binary signal, that represents a numerical evaluation of the overall magnitude of the input set of digital signals (thereby providing a numerical evaluation of the magnitude of the analog signal for the pixel). The output of a signal processor may be referred herein as "data", and may be stored in memory. This data may represent a floating point number or integer, for example.

Data from reading an array may be raw data (such as fluorescence intensity readings for each feature in one or more color channels, or, for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

A set of digital signals for a pixel (or an analog signal represented thereby) may be "saturated", "partially-saturated" or "non-saturated" depending on the number of saturated digital signals within the set. The digital signals in a saturated set of digital signals are all saturated, none of the digital signals in a non-saturated set of digital signals are saturated, and some but not all of the digital signals within a partially-saturated set of digital signals are saturated.

In certain embodiments, the methods provide "a set of non-saturated digital signals" and a "set of saturated digital signals", and processes the non-saturated digital signals to provide an evaluation of a pixel. In other words, the methods provide a means for distinguishing saturated and non-saturated signals, allowing only the set of non-saturated signals to be processed to produce an evaluation of a pixel. This is in contrast to prior art devices that do not discriminate between saturated and non-saturated signals, which are all processed be processed to produce an evaluation of a pixel.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "providing" encompasses such terms as "generating", "identifying" and "producing".

DETAILED DESCRIPTION OF THE INVENTION

Methods for producing data for a partially saturated pixel produced during scanning of a chemical array are provided. In general, an analog signal for a partially saturated pixel is sampled to obtain a set of non-saturated digital signals and a set of saturated digital signals. The saturated digital signals are then processed to produce data for the pixel. Also provided are computer program products comprising programming for performing the subject methods, and a chemical array scanner containing this programming. The invention finds use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, system and methods aspects of the invention are first described. This discussion is followed by a description of suitable hardware for use in the invention.

The following U.S. patent applications are herein incorporated by reference in their entireties for all purposes: Ser. No. 10/912,427, entitled: Multi-Gain Photodetection System for Array Analysis, filed Aug. 4, 2004; Ser. No. 10/912,463, entitled: "Detection of Feature Boundaries Pixels During Array Scanning", filed Aug. 4, 2004; and Ser. No. 10/912,027, entitled: "Filtering of Pixel Signals During Array Scanning", filed Aug. 4, 2004. The following published U.S. patent applications are incorporated by reference in their entirety, including all definitions, for all purposes: Ser. No. 10/086,932 (filed on Feb. 28, 2002 and published as 20030165871), Ser. No. 10/261,563 (filed on Sep. 30, 2002 and published as 20040064264), Ser. No. 10/212,191 (filed on Jul. 31, 2002 and published as 20040023224), Ser. No. 10/210,848 (filed on Jul. 31, 2002 and published as 20040021911), Ser. No. 10/137,658 (filed on Apr. 30, 2002 and published as 20030203371) and Ser. No. 10/086,658 (filed on Feb. 28, 2002 and published as 20030168579).

Methodology

As discussed above, the invention provides a method for evaluating (e.g., producing a numerical evaluation of the brightness of) a partially saturated pixel, where a "partially saturated pixel" is a pixel represented by a signal that is at least partly saturated, e.g., at least one of the digital samples of the signal is at a maximum amplitude. In general, partially saturated pixels correspond to bright areas of a scan of the surface of an object, e.g., a chemical array.

An illustration of a signal for a partially saturated pixel is shown as element 10 in FIG. 1. In general, such a signal is generated by a light detector and is an analog signal that changes in amplitude proportionally to the amount of light entering the detector. In certain embodiments, the detector is a photomultiplier tube (PMT). The signal may be an electrical signal and either the current or the voltage of the signal may vary in amplitude proportionally to the amount of light entering the detector. In certain embodiments it is the current of the signal that varies in amplitude according to the amount of light detected by the detector, and a "current-to-voltage" converter may be employed to convert this current signal to a voltage signal.

The graphs shown in FIG. 1 plot signal amplitude (i) versus time (t) for a pixel, which, in this figure, is period of time that a light signal is detected. Graph 2 shows an exemplary light signal 6, relative to the maximum intensity of light detectable by the detection system 4 (including a detector and, in certain embodiments other circuitry such as a current-to-voltage converter and/or a voltage amplifier). Some of the light signal is above the detection limit of the detection system. This light enters a detection system, and the detection system outputs an analog signal 10, as shown in graph 8. As noted in graph 8, part of the analog signal is maximal and "flat", indicating that the signal is saturated. In other words, in this example, the signal output of the detection system is partially saturated (i.e. saturated during a portion of the total pixel signal time). Saturated signals may be produced by any detection system component, e.g., a detector, a converter (e.g., a current to voltage converter or an analog-to-digital converter) or a signal amplifier, for example, depending on the dynamic range of the component, its gain, and the size of the input signal.

Figure 2:
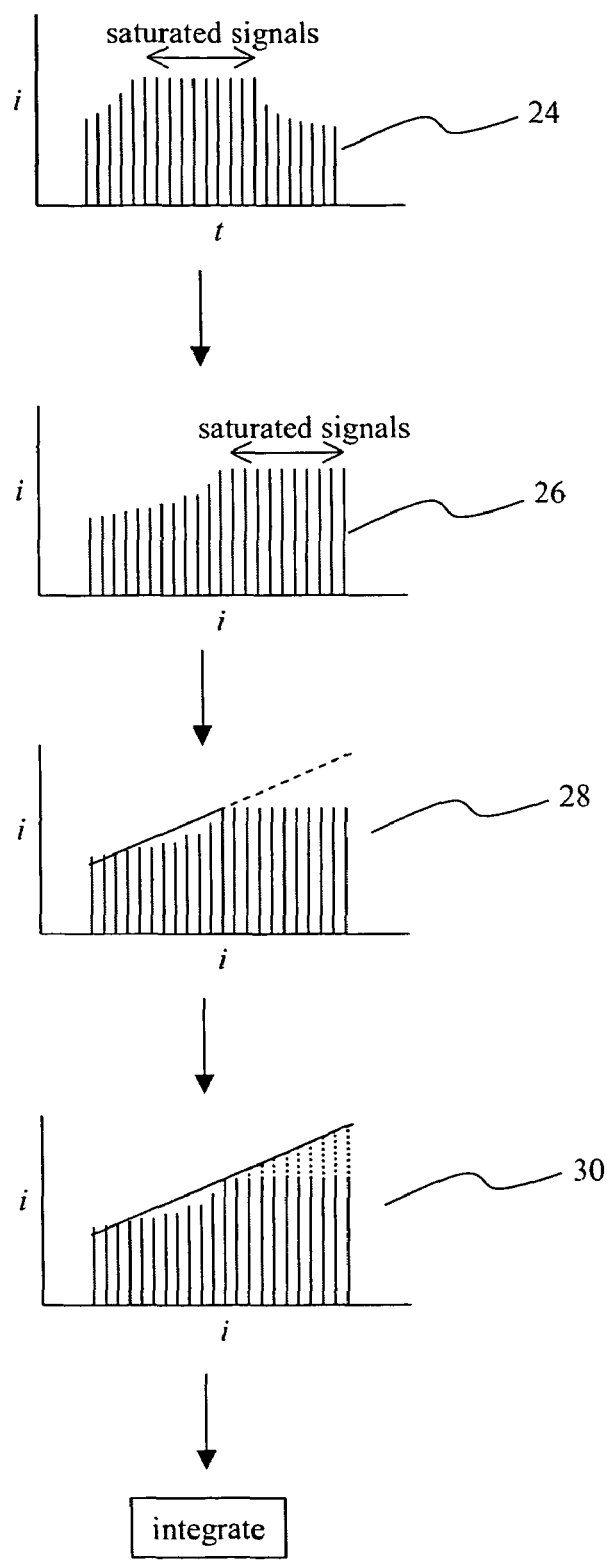
FIG. 2 schematically illustrates one example of a signal integration method that may be used in the subject methods.

Also referring to FIG. 2, analog signal 10 is then usually input into an analog-to-digital converter (A/D converter), and the A/D converter samples the analog signal 10, and outputs binary numbers via $2^n$ signal lines 16, where N is the number of signal lines, and output values range from 0 to $2^n-1$. How an analog signal is converted into a set of digital signals is illustrated in graph 12. The digital signals output by the A/D converter 16 are input into a digital signal processor which performs signal integration. For partially saturated pixels, the signal processor processes the non-saturated signals to produce an evaluation of the pixel, e.g., data for the pixel. In certain embodiments, the processing involves estimating the magnitude of any saturated signals by extrapolating from the non-saturated signals and integrates the estimated saturated signals and non-saturated signals to produce an evaluation of the pixel. For example, each pixel is usually associated with a numerical value, e.g., an integer or floating point number, representing the integrated scan signal from a region on the surface of an object (e.g., an array). This evaluation may be stored in memory. The time period corresponding to a pixel may be adjusted to correspond to any specified dimension representing a region of the surface of an object being scanned (e.g., such as a chemical array).

As noted above, one feature of the invention relates to the integration of partially saturated digital signals by the signal processor. In general, if a set of digital signals for a partially saturated signal for a pixel, i.e., a set of saturated digital signals and a set of non-saturated digital signals for the pixel, is input into the signal processor, the processor processes the non-saturated digital signals (e.g., will estimate the saturated digital signals for the saturated signals by extrapolating the non-saturated signals). The output signal of the signal processor represents a processed (e.g., integrated) version of the input digital signals.

In general, the principles of data extrapolation are well known in the mathematical and statistical arts and need not be discussed here in any great detail. In certain embodiments, such methods generally involve generating a line or curve of best fit for the available data points (i.e., the non-saturated signals), and extrapolating or extending that line to provide an estimate of other data points (i.e., the saturated signals). Such extrapolations may take into consideration a variety of tangible variables, such as the typical distribution of signal amplitudes for non-saturated pixels, the number of samples representing the partially saturated pixel, and the variability of signal amplitude for a partially saturated pixel, for example. In certain embodiments, particularly those embodiments in which the central pixel signals of a feature are fully saturated, those pixel signals can be estimated by extrapolating the numerical evaluations of the non-central pixels of the feature. An example of such methods, shown in FIG. 2, illustrates one methodology that may be employed.

Referring to FIG. 2, the digital signals representing a partially-saturated pixel are shown in element 24, in order of the time that they were obtained by the A/D converter. In one exemplary embodiment, in order to perform the methods discussed above, a digital signal processor may first order the digital signals by their size. This is illustrated in graph 26. Since the saturated signals will be the largest signals of the set of signals for a pixel, they will lie at the one of the ends of the ordered signal lines. A line representing the amplitude of the non-saturated signals may then be drawn, and that line may extended over the saturated pixels (represented by the solid and dotted line in graph 28). The saturated digital signals can be estimated according to where they intersect with this extended line. This is illustrated in graph 30, and the non-saturated and the estimated saturated signals can be integrated by the digital signal processor to provide data, i.e., an evaluation of the intensity of light for that pixel. Because the saturated signals have been estimated from an extrapolation of the non-saturated signals, this evaluation more accurately reflects the true intensity of light for a partially-saturated pixel. The foregoing example represents only one straightforward example of how non-saturated signals may be estimated by extrapolation, and, since many methods of extrapolation are known in the art, this example should not limit the claimed invention. Further, given that the above extrapolation methods are usually performed by a computer, the signal lines may not be ordered as they are described above, and the line of best fit may be expressed as a mathematical formula, etc.

The methods find most use in integrating signals for pixels that are partially saturated, i.e., the signal for a pixel is usually more than about 1% saturated, and usually less than 99%, less than about 95%, less than about 90%, less than about 80%, less than about 70%, less than about 60%, less than about 50%, less than about 40%, less than about 30%, less than about 20%, less than about 20%, less than about 10%, less than about 5% saturated. Saturated signals may be detected by virtue of the fact they are at maximal magnitude. Non-saturated signals may be detected because they are not at maximal magnitude.

As would be recognized in the art, the methods may be used more reliably if more digital signals per pixel, i.e., samples, are extrapolated and integrated. Although there is theoretically no limit to the number of times a signal for a pixel can be sampled, in general, each signal for a pixel is sampled at least about 10, at least about 20, at least about 50, at least about 100, at least about 200, at least about 500, at least about 1000, at least about 2000, at least about 5000, or at least about 10,000 times or more, usually up to at least about 100,000 times, or more, in a given time period corresponding to the pixel.

In certain alternative embodiments, a pixel signal may by estimated by averaging the non-saturated samples of the pixel and calculating the percentage of the pixel samples that are saturated. These figures, in combination, provide a means for estimation because, in general, the more samples that are saturated and the higher the average of non-saturated samples, the greater the estimated signal. In other words, if most of the samples of a pixel are saturated and the average non-saturated pixel value is close to that of a saturated pixel, the amount by which that pixel may be adjusted will be higher than if most of the samples of the pixel are non-saturated and the average non-saturated pixel value is well below saturation. In these embodiments, the relationship between the average value of the non-saturated pixels, the percentage of saturated pixels, and the amount by which a pixel signal should be adjusted can be experimentally determined (e.g., by scanning areas of known brightness to provide partially-saturated pixels that can be evaluated).

Any data for a pixel produced by the instant methods may be tagged as derived from a partially saturated pixel. In certain embodiments, the tag may indicate the percentage of saturated samples associated with the pixel signal. In particular embodiments, such tags may be present in unused bits of output from a subject processor. In other words, 1, 2, 3 or 4 or more bits of the output of a multi-bit output processor (e.g., a 16 or 24 bit output processor) may be used as a tag, whereas the remainder of the bits may be used to code a numerical evaluation (i.e., an integrated numerical evaluation) of the intensity of a pixel.

In certain embodiments, the subject methods may be done in "real-time". In other words, the single integrated signal or data for a pixel obtained using the subject methods is generally output from the processor prior to processing of the signals for the next pixel. In particular embodiments for example, data obtained from a signal may be stored in a buffer and analyzed while accumulating data from a future pixel, e.g., the next pixel scanned.

Figure 3:
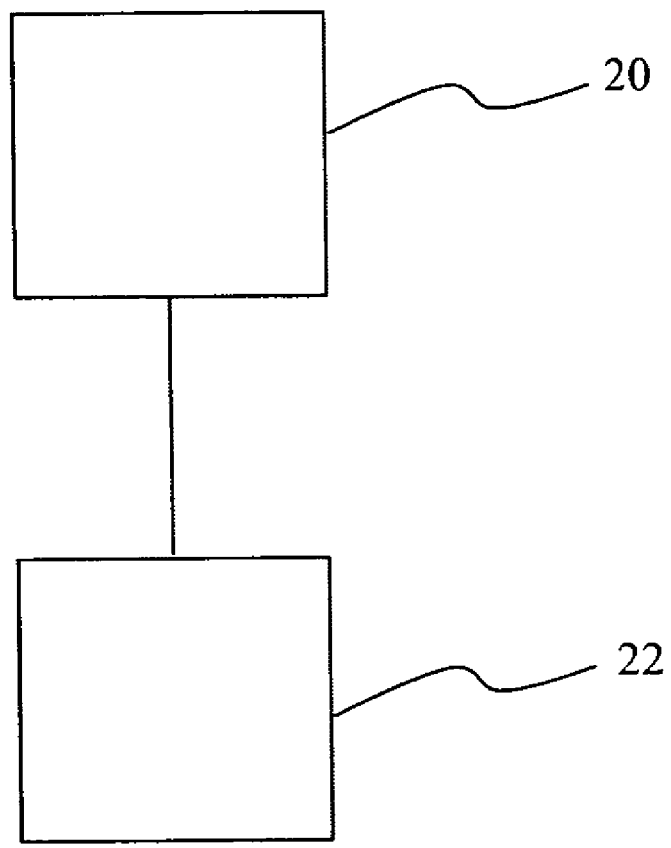
FIG. 3 schematically illustrates a system for performing the subject methods.

Accordingly, in view of the foregoing, the invention provides a system for performing the subject methods. This system is illustrated in FIG. 3. In general, the subject system contains at least a) an A/D converter 20 for sampling an analog signal for a pixel and provide a set of digital signals for that pixel, b) a digital signal processor 22 that is programmed to perform the subject methods and output data for a partially saturated pixel. Depending on how the system is configured, other system components may be present in the system, such as a current-to-voltage or voltage-to-current integrator, or the like.

Computer-Related Embodiments

The invention also provides a variety of computer-related embodiments. Specifically, the methods described above may be implemented through the execution of instructions stored in a computer program product in the form of programming, and the programming may be executed by a signal processor. Accordingly, the invention provides a digital signal processor programmed to estimate, adjust and integrate saturated digital signals by extrapolating non-saturated digital signals, as discussed above. The programming may be coded onto computer-readable medium, and the programming and the processor may be part of a computer-based system.

In certain embodiments, the above methods are coded onto a computer-readable medium in the form of "programming" or "programming product", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

Optical Scanners

While useful in any light detecting device (e.g., any optical scanner) that has a digital output, e.g. a digital camera, a flat bed scanner, etc., the invention finds particular use in chemical array scanners. Accordingly, also provided by the subject invention are chemical array scanners that contain a system for performing the subject methods described above. Typically such scanners have a laser excitation system, a photo-detection system that produces an analog signal proportional to and representative of emitted light from the surface of an object (e.g., a biopolymer array), a data processing system as described above, and, usually, a storage medium for storing data produced by scanning. A subject scanner may also contain programming for executing the subject methods.

The subject systems and methods find particular use in biopolymer array scanners. Accordingly, also provided by the subject invention is a biopolymer array scanner that contains a system for performing the subject methods described above. Typically, such scanners have a laser excitation system for emitting light from the surface of a chemical array, hardware for performing the methods described above, and, usually, a storage medium for storing data produced by scanning. A subject scanner may also contain programming for executing the subject methods.

Any optical scanner or device may be provided to include the above programming. Representative optical scanners of interest include those described in U.S. Pat. Nos. 5,585,639; 5,760,951; 5,763,870; 6,084,991; 6,222,664; 6,284,465; 6,329,196; 6,371,370 and 6,406,849—the disclosures of which are herein incorporated by reference. An exemplary optical scanner as may be used in the present invention is shown in FIG. 4.

Figure 4:
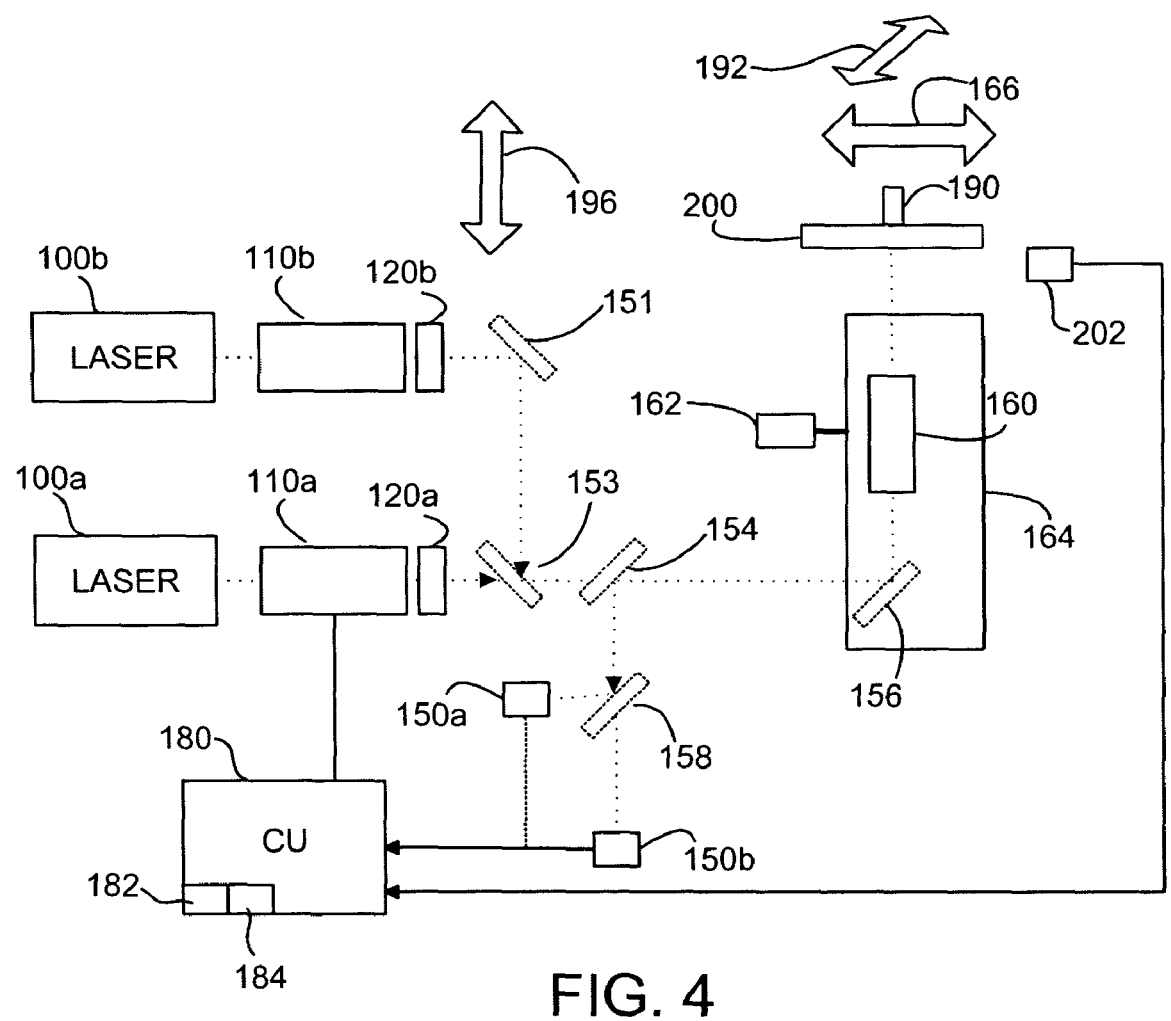
FIG. 4 schematically illustrates an apparatus as may be used in the invention.

Referring now to FIG. 4, an exemplary apparatus of the present invention (which may be generally referenced as an "array scanner") is illustrated. A light system provides light from a laser 100 which passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 111a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150a and 150b.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT), or photodiode or avalanche photodiode device (APD), such as a charge-coupled device (CCD), a charge-injection device (CID), or a complementary-metal-oxide-semiconductor detector (CMOS) device). All of the optical components through which light emitted from an array 12 or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 4 to a position at an end of a next line, and repeating the line scanning and transitioning until the entire array has been scanned.

This scanning feature is accomplished by providing a housing 164 containing mirror 158 and focuser 160, which housing 164 can be moved along a line of pixels (i.e., from left to right or the reverse as viewed in FIG. 4) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 4 may further include a reader (not shown) which reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

The system may also include detector 202, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, autofocus system 202 may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415, 184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150a, 150b (these different signals being different "channels"), namely a signal which results at each of the multiple detected wavelengths from emitted light for each scanned region of array 12 when at the reading position mounted in holder 200. Controller 180 also receives the signal from autofocus detector 202, and provides the control signal to EOM 110, and controls the scan system. Controller 180 contains all the necessary software to detect signals from detector 202, and regulate a motorized or servo-controlled adjuster 190 through a control loop. Controller 180 may also analyze, store, and/or output data relating to emitted signals received from detectors 150a, 150b in a known manner.

Controller 180 also includes a programmable digital signal processor for performing the digital signal integration methods described above, and usually include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with the partially-saturated pixel-processing methods described above, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

While it is noted that a scanner that reverses scanning direction at the end of each scan line (i.e. a bi-directional scanner) is disclosed, unidirectional scanners also find use with the methods of the invention.

Utility

The subject array scanners find use in a variety applications, for example, such as in analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288, 644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. Certain embodiments of the invention may involve transmitting data obtained from a method described above from a first location to a remote location. Certain other embodiments of the invention may involve receiving, from a remote location, data obtained from a method described above.

In reading the array, any partially-saturated pixels are usually processed using the methods described above.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

Kits

Kits for use in connection with the subject invention may also be provided. Such kits usually include at least a computer program product comprising computer readable medium including programming as discussed above and, in certain kits, instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject programming and instructions, the kits may also include one or more reference arrays, e.g., two or more reference arrays for use in testing an optical scanner after software installation.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing data for a partially saturated pixel during scanning of a chemical array, comprising:
    sampling an analog signal for a partially saturated pixel to provide a set of non-saturated digital signals and a set of saturated digital signals;
    extrapolating said non-saturated digital signals to provide a set of estimated digital signals for said saturated digital signals;
    integrating said non-saturated digital signals and said estimated digital signals to produce data for said partially saturated pixel; and
    storing said data on a physical computer-readable medium in a user-readable format.

2. The method of claim 1, wherein said extrapolating comprises estimating said saturated digital signals by extrapolating from said non-saturated digital signals to provide a set of estimated digital signals.

3. The method of claim 1, wherein said chemical array is a nucleic acid array.

4. The method of claim 1, wherein said analog signal for a partially saturated pixel is sampled at least 10 times.

5. The method of claim 1, further comprising employing a current to voltage converter that converts an analog current representing intensity of said pixel to an analog voltage signal.

6. The method of claim 1, further comprising tagging said data with an identifier to indicate that said data is derived from a partially saturated pixel.

7. The method of claim 1, further comprising storing said data on a computer-readable medium.

8. A method of assaying a sample, said method comprising:
    (a) contacting said sample with a chemical array of two or more chemical ligands immobilized on a surface of a solid support; and
    (b) employing the method of claim 1 to obtain data.

9. The method according to claim 8, wherein said employing step (b) includes:
    sampling a partially saturated analog signal to provide a set of non-saturated digital signals and a set of saturated digital signals; and
    extrapolating said non-saturated digital signals to provide a set of estimated digital signals; and
    integrating said non-saturated digital signals and said estimated digital signals to produce data for said partially saturated pixel.

10. The method of claim 9, wherein said extrapolating comprises estimating said saturated digital signals by extrapolating said non-saturated digital signals to provide a set of estimated digital signals.

11. The method of claim 8, wherein said chemical array is a nucleic acid array.

* * * * *

UNITED STATES PATENT AND TRADEMARK OFFICE
CERTIFICATE OF CORRECTION

| | | |
|---|---|---|
| PATENT NO. | : 7,877,212 B2 | |
| APPLICATION NO. | : 10/912661 | |
| DATED | : January 25, 2011 | |
| INVENTOR(S) | : Kenneth L. Staton et al. | |

It is certified that error appears in the above-identified patent and that said Letters Patent is hereby corrected as shown below:

On the Title page, in field (56), under "Other Publications", in column 2, line 1, delete "Alogorithm" and insert -- Algorithm --, therefor.

On the Title page, in field (56), under "Other Publications", in column 2, line 2, delete "Spcetral" and insert -- Spectral --, therefor.

In column 18, line 21, in Claim 1, after "a" delete "physical".

Signed and Sealed this
Twenty-sixth Day of July, 2011

David J. Kappos
*Director of the United States Patent and Trademark Office*